United States Patent
Tate, Jr.

(10) Patent No.: US 9,500,648 B1
(45) Date of Patent: Nov. 22, 2016

(54) RAPID LYME ANTIGEN TEST FOR DETECTION OF LYME DISEASE

(71) Applicant: Robert M. Tate, Jr., Montgomery, AL (US)

(72) Inventor: Robert M. Tate, Jr., Montgomery, AL (US)

(*) Notice: Subject to any disclaimer, the term of this patent is extended or adjusted under 35 U.S.C. 154(b) by 122 days.

(21) Appl. No.: 14/061,659

(22) Filed: Oct. 23, 2013

(51) Int. Cl.
  *G01N 33/554* (2006.01)
  *G01N 33/569* (2006.01)

(52) U.S. Cl.
  CPC .............................. *G01N 33/56911* (2013.01)

(58) Field of Classification Search
  None
  See application file for complete search history.

(56) References Cited

U.S. PATENT DOCUMENTS

| | | |
|---|---|---|
| 4,774,177 A | 9/1988 | Marks |
| 4,888,276 A | 12/1989 | Shelburne |
| 4,931,385 A | 6/1990 | Block et al. |
| 5,217,872 A | 6/1993 | Dorward et al. |
| 5,403,718 A | 4/1995 | Dorward et al. |
| 5,780,041 A | 7/1998 | Simpson et al. |
| 6,475,492 B1 | 11/2002 | Philipp et al. |
| 2004/0033623 A1* | 2/2004 | Shah et al. ................. 436/518 |
| 2013/0085076 A1 | 4/2013 | Douglas et al. |

OTHER PUBLICATIONS

Package insert for Multiplex Lyme disease test 2007.*
Aguero-Rosenfeld et al. ( Clinical Microbiology Reviews, vol. 13, No. 3, pp. 484-509, 2005).*
An Introduction to EISA ELISA base procedure ABD Serotec brochure. from internet Dates ack to 1970.*
Harris, NS and Stephens BG, Detection of Borrelia burgdorferi Antigen in Urine from Patients with Lyme Borreliosis, Journal of Spirochetal and Tick-Borne Diseases, vol. 2, No. 2; 1995, http://www.igenex.com/luatart.htm.

* cited by examiner

*Primary Examiner* — Ja'na Hines
*Assistant Examiner* — Khatol Shahnan Shah
(74) *Attorney, Agent, or Firm* — Baxam Law Group, LLC; Deanna L. Baxam

(57) ABSTRACT

A method for detecting *B. burgdorferi* antigens in body fluid samples, such as urine. Polyclonal antibodies are used that bind to 31, 34, and 39 kDa *B. burgdorferi* antigens, wherein the polyclonal antibodies function as immobilized capture antibodies. Detection antibodies are used, having an enzyme linked thereto, which also bind to the *B. burgdorferi* antigens. A body fluid sample is reacted with the detection antibodies to form complexes between the detection antibodies and the *B. burgdorferi* antigens in the body fluid sample. The complexes are reacted with the immobilized capture antibodies, wherein the complexes become linked to the capture antibodies. A substrate is added to the complexes linked to the capture antibodies, wherein the substrate is converted by the enzyme to a visual and/or detectable product if *B. burgdorferi* antigens are present in the body fluid sample.

10 Claims, 2 Drawing Sheets

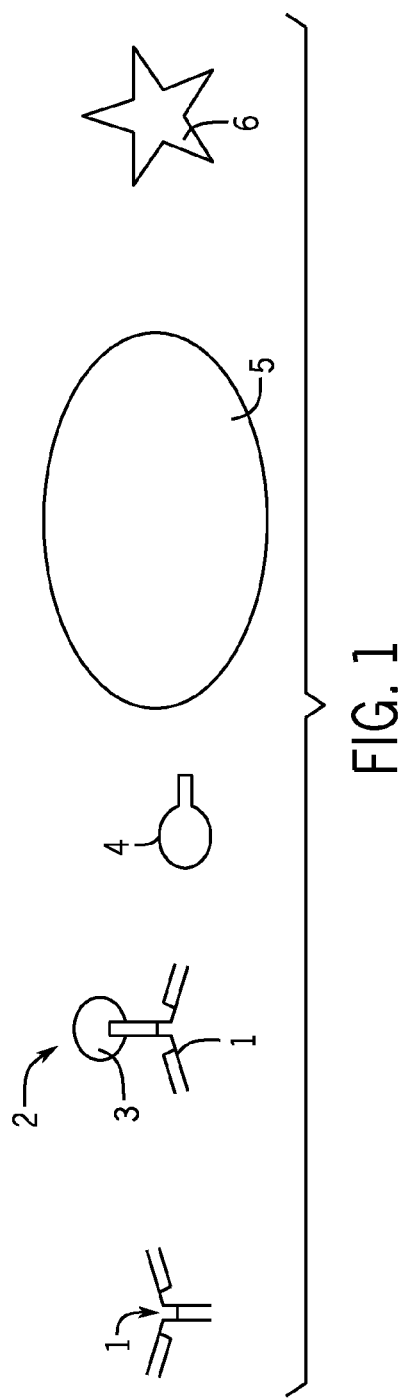
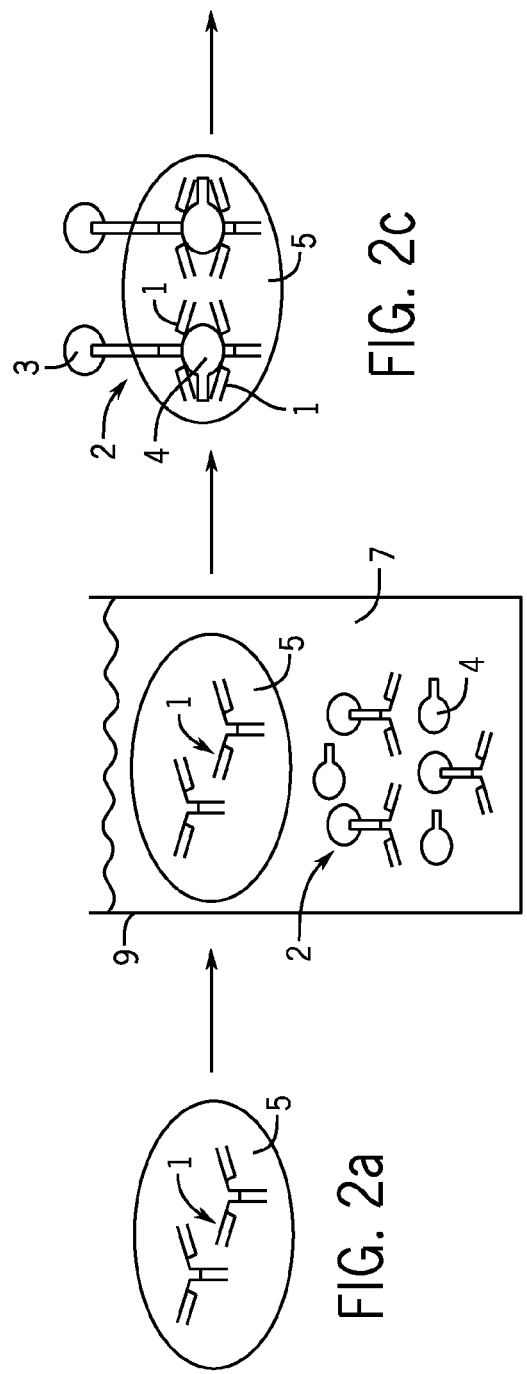
FIG. 1
FIG. 2a
FIG. 2b
FIG. 2c

RAPID LYME ANTIGEN TEST FOR DETECTION OF LYME DISEASE

CROSS REFERENCE TO RELATED APPLICATIONS

This application claims the benefit of priority from U.S. Provisional Applications No. 61/777,626 filed Mar. 12, 2013, No. 61/794,637 filed Mar. 15, 2013, and No. 61/820,406 filed May 7, 2013.

FIELD OF THE INVENTION

This invention relates to tests for detecting antigens and, more particularly, to a rapid ELISA test for detecting *B. burgdorferi* antigens in bodily fluids for the diagnosis of Lyme disease.

BACKGROUND OF THE INVENTION

Lyme disease is a bacterial infection caused by the spirochete *Borrelia burgdorferi* (*B. burgdorferi*) which is transmitted to patients through the bite of a blacklegged tick that remains attached to the patient for 24-36 hours. Symptomatically, early Lyme disease presents itself with flu-like symptoms causing the patient to experience body-wide itching, chills, fever, headache, muscle pain, and stiffness in the neck. Lyme disease is distinguished through the appearance of an erythema migrans, circular red rash around the bite area that resembles a "bull's eye". Through early detection and immediate antibiotic treatment, Lyme disease can be completely cured. Although immediate antibiotic treatment has shown to completely cure patients of Lyme disease, the administration of the antibiotic treatment during the critical early stages of the disease is greatly dependent on an accurate diagnosis.

Misdiagnosis of Lyme disease often occurs as a result of a misinterpretation of the patient's clinical symptoms. In addition, Lyme disease exacerbates the diagnostic process by causing variability in the patient's immune response during the early stages of infection. The variability in the immune response can produce false negatives in serum antibody detection assays, such as immunofluorescent assays (IFA), enzyme-linked immunosorbent assays (ELISA), and Western Blot assays. These immunoassays utilize serum derived *B. burgdorferi* antigens to detect the presence of specific antibodies in a patient's body fluids. Due to the variability in the immune response during the early stages of infection, these antibody detection based assays are unable to detect the *B. burgdorferi* antibodies that are below a threshold concentration for detection. This inability to detect *B. burgdorferi* antibodies at the early stages of infection results in misdiagnosis that results in delayed administration of antibiotic treatments.

This antibody diagnostic detection approach has been found not to work as well with Lyme disease as with many other infectious diseases. One of the reasons for this is that only a low number of spirochetes is present and that it is hard for the immune system of the infected organism to detect the anitgens in the outer membrane of the spirochetes. Another reason is that the antibody response to the *B. burgdorferi* infection first arises weeks after the bite of the tick, and in many cases first after the patient has shown clinical signs of the disease.

An enzyme-linked immunosorbent assay (ELISA) has been used to detect antibodies in the blood of individuals with Lyme disease. This method uses a *B. burgdorferi* commercial antigen attached to a support. The antibody in the blood is reacted with this antigen and allowed to bind to the antigen. The resulting antigen-antibody is incubated with an enzyme-labeled anti-antibody which will bind to the antibody of the antigen-antibody complex. An enzyme substrate is then added. The enzyme on the anti-antibody will convert the substance to a product, and the amount of product is measured or detected, for example, visually. The enzyme activity of converting the substrate to a product is related to the amount of antibody bound to the antigen, thus indicating the amount of antibody in the blood and the presence of Lyme disease. Enzyme immunoassays have been desirable because the direct visualization of an antigen-antibody complex is thereby possible, using the product as a chromogenic indicator. This test can give false negatives if the concentration of antibodies is too low or the antibodies do not react well with the commercial antigens A dot-immunobinding ELISA assay has also been developed. The principle of this type of assay is as follows: A dilute solution or suspension of commercial antigen is "dotted" on to a white, nitrocellulose piece of filter paper. The dot is then incubated with a first antibody from the blood of an infected patient and with a peroxidase enzyme-conjugated anti-antibody directed against the first antibody. After the enzymatic action of the peroxidase on a substrate, a product is formed and detected as a colored dot against the white filter paper background. This test can also give false negatives if the concentration of antibodies is too low or the antibodies do not react well with the commercial antigens.

Although it may take time for antibodies to develop in response to a *B. burgdorferi* infection, the presence of antigens in bodily fluids, such as blood and urine, may occur much sooner. These antigens are exported (or shed) in vivo and the detection of these antigens is a means of diagnosing Lyme disease. The antigens are extracellular membrane vesicles and other bioproducts including the major extracellular protein. Two well-known antigens that develop in response to a *B. burgdorferi* infection are designated as OspA and OspB. OspA has a molecular weight of 31 kDa and OspB 34 kDa. These antigens, however, do not appear early after infection. A 39 kDa antigen does appear early after infection.

U.S. Pat. No. 5,217,872 discloses a method for detection of *B. burgdorferi* antigens in bodily fluids, such as urine, as a diagnostic test for the presence of Lyme disease. In this method polyclonal antibodies were raised in rabbits against membrane vesicles and against an 83 kDa major extracellular protein (MEP) of *B. burgdorferi*. These antibodies were produced by rabbits in response to immunization with purified antigens, and the antibodies were purified by affinity chromatography. Immunized rabbits were periodically boosted with antigen suspended in dPBS. Sera were collected over a period of 10 weeks. Antibodies resulting from immunization with membrane vesicles served as capture antibodies. Antibodies resulting from immunization with MEP served as detection antibodies. The capture antibodies are bound to an inert solid support. A body fluid sample of an infected patient is brought into contact with this solid support under conditions conducive for the formation of immune complexes between the capture antibodies and antigens associated with *B. burgdorferi* in the body fluid sample. The solid support is washed and then brought into contact with detection antibodies under conditions conducive to formation of immune complexes consisting of the capture antibody, the antigens, and the detection antibody. The solid support with its immune complexes can be washed and then the antigen/capture antibody portion of the complex is detected by means well known in the art. Preferably, the detection antibody is conjugated with the enzyme horseradish peroxidase and detected by chromogenic assay. The capture antibodies recognize B. burgdorferi antigens at 11, 14, 22, 31, and 34 kDa in human urine in this assay. There is no evidence that the capture antibodies recognize the 39 kDa antigen in this assay.

It would be desirable to provide a diagnostic tool which is able to diagnose a B. burgdorferi infection at all stages, including at very early stages even before the clinical signs of infections appear. There exists a need for a reliable, rapid, inexpensive and non-invasive method for the diagnosis of Lyme disease. There are many situations in the diagnosis and treatment of Lyme disease where even a reliable test having a low level of false positives or negatives would be extremely valuable by itself, and particularly if used in conjunction with other tests that could be used to eliminate the false positives or negatives, or with clinical findings to identify the true positives.

SUMMARY OF THE INVENTION

This invention provides a method for detecting B. burgdorferi antigens in body fluid samples in order to diagnose the presence of Lyme disease in patients infected with the spirochete B. borgdorferi. Polyclonal antibodies that bind to 31, 34, and 39 kDa B. burgdorferi antigens are provided. These antibodies are immobilized on a solid support to function as capture antibodies. Detection antibodies having an enzyme linked thereto are provided. The detection antibodies are able to bind to the B. burgdorferi antigens. A body fluid sample is reacted with the detection antibodies to form complexes between the detection antibodies the said B. burgdorferi antigens in the body fluid sample. The complexes are reacted with the capture antibodies on the solid support, wherein the complexes become linked to the capture antibodies. A substrate is added to the complexes linked to the capture antibodies, wherein the substrate is converted by the enzyme to a visual and/or detectable product if B. burgdorferi antigens are present in the body fluid sample.

The method may be implemented by having the detection antibodies in a first container and the chromogenic substrate in solution in a second container. The body fluid sample is placed in the first container and then the solid support is placed in the body fluid sample in the first container. The solid support is removed from said first container, washed, and placed in the solution in the second container. A visible and/or detectable color is produced in the second container by the action of the enzyme on the chromogenic substrate if the B. burgdorferi antigens are present in the body fluid sample. Preferably, the polyclonal antibodies are derived from animals hyper immunized with low passage strain B31 of B. burgdorferi, the enzyme is horseradish peroxidase, the chromogenic substrate is tetramethylbenzidine, and the detection antibodies in the second container are lyophilized.

In an alternant embodiment, the assay of the invention is performed using a capillary membrane lateral flow test assay strip. The capillary membrane lateral flow test assay strip has a first end, a second opposite end, a reaction zone near the first end, and a test zone near the second opposite end. The reaction zone has detection antibodies contained therein. The detection antibodies are able to bind to 31, 34, and 39 kDa B. burgdorferi antigens and the detection antibodies are linked to an enzyme. The test zone has capture antibodies immobilized thereon. The capture antibodies are polyclonal antibodies and are able to bind to said B. burgdorferi antigens. The test zone also has a chromogenic substrate therein. A body fluid sample is placed on the first end of the assay strip. The body fluid sample migrates into the reaction zone, wherein the detection antibodies bind to the B. burgdorferi antigens in the body fluid sample, thereby forming antigen-detection antibody complexes. Thereafter, the body fluid sample migrates into the test zone, wherein the body fluid sample contains the antigen-detection antibody complexes. The antigen-detection antibody complexes become linked to the capture antibodies, thereby causing the enzyme to convert the chromogenic substrate to a visible and/or detectable colored product if the B. burgdorferi antigens are present in the body fluid sample. Preferably, the polyclonal antibodies are derived from animals hyper immunized with low passage strain B31 of B. burgdorferi, the enzyme is horseradish peroxidase, and the chromogenic substrate is tetramethylbenzidine, An advantage of the present invention are polyclonal antibodies that bind to the 31, 34, and 39 kDa B. burgdorferi antigens.

Another advantage is the ability to detect the presence of B. burgdorferi antigens in the urine, and other bodily fluids, of patients infected with Lyme disease thereby providing a diagnosis of Lyme disease.

Another advantage is a method for diagnosing the presence of Lyme disease at very early stages, even prior to the occurrence of clinical symptoms.

Another advantage is a method for monitoring the effectiveness of antibiotic treatment in patients with Lyme disease.

Another advantage is a rapid, simple test for detecting Lyme disease by detecting the presence of B. burgdorferi antigens in the urine, wherein the test can be performed in a user's home.

BRIEF DESCRIPTION OF THE DRAWINGS

FIG. 1 illustrates the various components of the B. burgdorferi antigen detection assay of the invention.

FIGS. 2a-2d show an assay method of the invention for B. burgdorferi antigens in bodily fluids.

DETAILED DESCRIPTION OF THE INVENTION

Figure 2D:
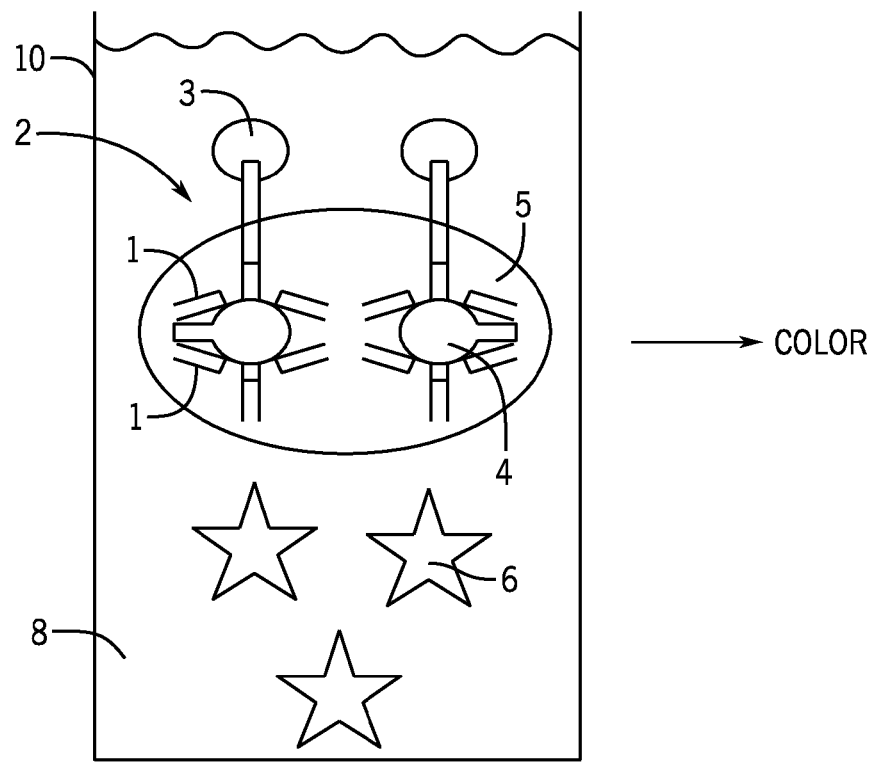

While the following description details the preferred embodiments of the present invention, it is to be understood that the invention is not limited in its application to the details of construction and arrangement of the parts illustrated in the accompanying figures, since the invention is capable of other embodiments and of being practiced in various ways.

The present invention provides an assay for B. burgdorferi antigens. The assay detects the presence of these antigens in the body fluids of infected individuals during the critical early stages of the infection as well as during the chronic stages of the infection. The present invention accomplishes this through the use of a polyclonal antibody that reacts to B. burgdorferi antigens found during all stages of infection in the patient's urine. The polyclonal antibodies utilized by the present invention have reactivity with the 31, 34, 39, and 93 kDa antigens of B. burgdorferi. The specificity of the polyclonal antibodies for these antigens allows for the detection of low levels of antigens, thereby providing a low incidence of false negatives. This assay can be implemented in the form of a rapid immunoassay kit that is able to detect the presence of the specific antigens through a single use disposable test strip.

The polyclonal antibody is derived from a pool of test rabbits hyper immunized with sonicated, low passage strain B31 of *B. burgdorferi*. When tested against positive samples this polyclonal antibody was determined to react with antigenic moieties that weighed 31, 34, 39, and 93 kDa. While the reactivity against 31 and 34 kDa was expected, the reactivity of the polyclonal antibody with the 39 kDa antigen was unexpected. Tests were performed to explore the possibility of interference but results were negative. Furthermore the 39 kDa antigen was found present in all stages of Lyme disease. Due to the detection of this distinct antigenic moiety present during the early stages of Lyme disease, plus the known 31 (OspA) and 34 (OspA) kdA antigens, this polyclonal antibody was selected as the optimal component for capturing the *B. burgdorferi* antigens for diagnosing Lyme disease.

The method of this invention is used to detect the presence of the 31, 34, 39, and 93 kDa antigens in a biological sample, such as urine, suspected of containing one or more of those antigens. For this purpose a solid support, preferably a nitrocellulose support or a plastic polymer support, is pre-impregnated with the polyclonal antibody (first antibody) described above specific for the 31, 34, 39, and 93 kDa antigens. This polyclonal antibody is immobilized on the solid support and acts as a capture antibody. A patient body fluid sample, such as urine, and an enzyme conjugate of the polycolonal antibody (second antibody), which acts as a detection antibody, are then added to the solid support. If *B. burgdorferi* antigens are present in the patient body fluid sample, the antigens, having multiple binding sites, are bound immunologically to both capture antibody and the detection antibody. After addition of a substrate for the conjugated enzyme, a distinctly colored reaction product is formed, but only if the support contains immunologically immobilized enzymes. The enzymes will be immobilized if there are *B. burdorferi* antigens in the patient body fluid sample because the antigens will link the capture antibody to the detection antibody.

In a general description of the assays of the invention, antigens in a patient body fluid sample are reacted with detection antibodies to form antigen-detection antibody complexes. The antigen-detection antibody complexes are reacted with immobilized capture antibodies and a chromogenic substrate. The antigen binds the detection antibodies to the capture antibodies and the chromogenic substrate is then converted to a visible colored product indicating the presence of the antigens.

A diagnostic kit of this invention as described herein contains, preferably, (1) an antibody coated solid support; (2) a vial of lyophilized product containing antibody-enzyme conjugate; (3) a measuring dispenser such as an eye dropper; and (4) vials containing the active components of a chromogenic solution. Using the measuring dispenser, the user dispenses a required amount of body fluid sample (e.g. urine, suspected of containing the *B. burgdorferi* antigens) into the vial of the lyophilized product containing conjugate. The coated antibody solid support is immediately inserted into the vial containing the body fluid sample and lyophilized product and gently stirred to form a homogeneous mixture. The mixture is allowed to incubate for a prescribed period at room temperature between about 15 degrees C. to less than 37 degrees C. The antibody coated solid support is removed and washed with cold tap water and then immersed into the chromogenic solution. The user observes if there is a color change in the chromogenic solution which would indicate the presence of *B. burgdorferi* antigens in the body fluid sample.

The assay of this invention can also be performed with a lateral flow test assay on a capillary membrane strip. A body fluid sample is placed on one end of the test strip and migrates towards an opposite end of the strip by capillary action. The body fluid sample first engages lyophilized detection antibodies in a reaction zone where the antigens in the body fluid sample bind to the detection antibodies forming antigen-detection antibody complexes. The antigen-detection antibody complexes in the body fluid sample then engage capture antibodies immobilized in a test zone. The test zone also has a chromogenic substrate and when the antigen-detection antibody complexes engage the capture antibodies the chromogenic substrate is converted to a visible colored product.

It is noted that immunochemical detection protocols are well known in the art and optimized conditions for antigen detection can be determined with minor adjustments and without undue experimentation. For example, see U.S. Pat. No. 4,931,385 which is incorporated herein by reference.

In ELISA antibody sandwich assays for antigens, such as used herein, the first and second antibodies may be prepared in like manner from rabbit polyclonal antisera generated by inoculation of rabbits with low passage strain B31 of *B. burgdorferi*. The polyclonal antibodies are typically purified by gel chromatography and salt precipitation. These polyclonal antibodies may be used as both the first (capture) antibodies and the second (detection) antibodies. It should also be appreciated, however, that other binding materials such as lecithin can be used in place of either the first or second antibodies to coat the solid support or link the assay antigen to enzyme so long as the substance provides desired binding specificity.

A variety of structures and materials may be employed for the solid support. A solid phase is established by insolubilizing the assay reagents through bonding to the solid support. Suitable solid support materials include cellulose, cross-linked dextrose, silicon rubber, microcrystalline glass, and a wide variety of plastics. Suitable structures are preformed such as tubes, disks, strips, dip sticks, and microplates. The immunologically reactive components may be covalently bonded to the solid support, cross-linked, or physically coupled thereto. In the preferred embodiment the solid support comprises a nonporous injection molded polymer article. Polystyrene, polypropylene, polyvinyl chloride, polyamides, and other polymers have been widely employed in such applications, or styrene-acrylonitrile copolymer.

In coating the solid support, a procedure is adopted in accordance with the coating characteristics of the immunologically active material. Most substances will effectively coat by application in solution and incubation for a reasonably brief period. In a preferred embodiment the solid support, typically a dipstick, is coated with a first antibody at ambient conditions of between 15 degrees C. to less than 37 degrees C. to effect adsorption. The coated solid support is then treated with a blocking solution also at room temperature conditions of between 15 degree C. to less than 37 degree C. to block remaining adsorption sites and thus prevent nonspecific binding of immunologic reagents to the solid support surface.

The blocking solution may contain a blocking agent and a sugar component in physical admixture. The sugar component is preferably sucrose but can be selected from polysaccharides and oligosaccharides, including disaccharides as well as monosaccharides, provided the specie selected or any mixture containing different species of the above classes of sugars is water soluble. Examples of suitable monosaccharides are glucose and fructose. Examples of suitable disaccharides are sucrose, maltose, trehalose and lactose and a suitable saccharide mixture is dextrin. The blocking agent may be bovine serum albumin (BSA), gelatin, milk protein, or normal nonspecific IgG antibody, preferably bovine serum albumin and milk protein.

Suitable enzymes for conjugating to the second antibody include, for example, acetal cholinesterase, alkaline phosphatase, cytochrome C, B-D-glucoronidase, glucoamylase, B-D-galactosidase, glucose oxidase, lactate dehydrogenase, lactoperoxidase, ribonuclease, tyrosinase, and urease. The preferred enzyme is horseradish peroxidase (HRPO). The preferred conjugation method uses sodium periodate to form aldehyde groups in the peroxidase, which in turn react with the amino groups of the antibody to be labeled. The periodate oxidation may be carried out at low pH to reduce undesirable self-coupling of the HRPO molecules. The conjugates are then purified by methods known in the art, for example by molecular sieving as by gel chromatography; affinity chromatography; and salt precipitation. A wide variety of peroxidase substrates oxidized by $H_2O_2$ are available, preferably, tetramethylbenzidine (TMB). TMB in the presence of HRPO and $H_2O_2$ is converted to TMB-diimine which forms a visible blue color. Although the assay utilizes a colorimetric detection technique to measure the enzyme, it is possible to use a variety of optical detection techniques. Alternative techniques include, for example, ultraviolet radiation and fluorescence detection.

The conjugate is, preferably, contained within a lyophilized mixture (see U.S. Pat. No. 4,931,385). Briefly, polyethylene glycol, Hepes Salt, Hepes Acid, EDTA, magnesium sulfate crystalline, and dextrins are added to distilled water in effective amounts/concentrations. The solution is mixed until all of the above components are dissolved. Liquid surfactant is then added to the mixture. The resulting solution should have a final pH in the range of 7.2 to 7.5. The solution is then aseptically filtered. The antibody-enzyme conjugate (second antibody) is then added to the filtered solution resulting in a final lyophilization solution containing conjugate. This final lyophilization solution is then subjected to lyophilization by methods well known in the art to form the lyophilized product to be used in the assay.

FIG. 1 illustrates the various components of the Lyme antigen detection assay of the invention. The polyclonal antibody 1, derived from animals, such as rabbits, hyper immunized with low passage strain B31 of *B. burgdorferi*, is used as the capture antibody. This polyclonal antibody may also be used as an enzyme-conjugated detection antibody 2 having an enzyme 3 attached thereto. The 31, 34, 39, and 93 kDa antigens 4 are the antigens detected in body fluids of patients infected with *B. burgdorferi*. The solid support 5 is used to bind and immobilize the capture antibodies 1 thereto. The chromogenic substrate 6 is used to generate color when it is presented to enzyme 3 on the detection antibody 2. When the enzyme 3 is HRPO, hydrogen peroxide ($H_2O_2$) is made available to the enzyme.

FIGS. 2*a*-2*d* show an assay method of the present invention for *B. burgdorferi* antigens in bodily fluids. FIG. 2*a* shows a solid support 5, such as a dipstick, with capture antibodies 1 bound thereto. FIG. 2*b* illustrates a first container 9 having a lyophilized form of the detection antibody 2 contained therein. A patient body fluid sample 7, such as urine, is added to the container 9, thereby solubilizing the lyophilized antibody 2. If the patient is infected with Lyme disease the patient will have one or more of the 31, 34, 39, and 93 kDa antigens 4 in the urine 7. The antigens 4 will bind to the capture antibody 2, thereby immobilizing enzyme 3. The solid support 5 is removed from the first container 9, as shown in FIG. 2*c*. FIG. 2*c* also illustrates the antigen 4 bound to the capture antibody 1 and the detection antibody 2 on solid support 5. The solid support 5 is then washed with water and then inserted into second container 10 as shown in FIG. 2*d*. Second container 10 has a solution 8 with a chromogenic substrate 6 and $H_2O_2$ dissolved therein. Because enzyme 3 is now immobilized on solid support 5 enzyme 3 will, in the presence of $H_2O_2$, oxidize the chromogenic substrate 6 to a product which produces a visible color. If no antigens 4 are present in the urine 7, enzyme 3 will not be immobilized on the solid support 5, the chromogenic substrate 6 will not be oxidized, and no visible color will be produced. Thus, the production of color indicates the presence of the Lyme disease antigens in the patient body fluid sample and the patient is considered as infected with the Lyme disease. Accordingly, if no color is produced, the patient is considered as not infected with the Lyme disease.

Figure 3:
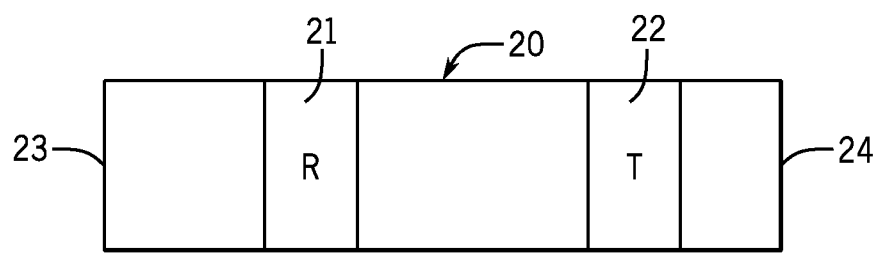
FIG. 3 illustrates the application of a lateral flow test assay method to the B. burgdorferi antigen assay of the invention.

The assay of this invention can also be implemented on a lateral flow test assay strip. The lateral flow test assay method is well-known in the art as is commonly used to test for human chorionic gonadotropin in the urine of women as a pregnancy test. FIG. 3 illustrates the application of this method to the *B. burgdorferi* antigen assay of the present invention. The capillary membrane lateral flow test assay strip 20 has a reaction zone 21 near a first end 23 and a test zone 22 near a second opposite end 24. The reaction zone 21 has detection antibodies contained therein. The detection antibodies are not immobilized on the assay strip 20. The test zone 22 has *B. burgdorferi* capture antibodies contained therein, plus a chromogenic substrate. The capture antibodies are immobilized on the capillary membrane assay strip 20. To test for the presence of *B. burgdorferi* antigens in the patient body fluids, such as urine, a portion of the patient body fluid is placed on the first end 23 of assay strip 20. The fluid migrates towards the second end 24. As the body fluid sample migrates it passes through the reaction zone 21 and *B. burgdorferi* antigens in the body fluid sample bind to the detection antibodies in reaction zone 21. As the fluid continues to migrate towards the second end 24 it carries the antigen-detection antibody complexes with it. As the fluid passes through the test zone 22 the antigens in the antigen-detection antibody complexes bind to the capture antibodies therein. This binding allows the enzyme in the detection antibodies to react with the chromogenic substrate to produce a visible colored product, indicating the presence of *B. burgdorferi* antigens in the body fluid sample. If there were no *B. burgdorferi* antigens in the body fluid sample then no color would be produced.

A diagnostic kit can be provided for performing the assay described in FIGS. 2*a*-2*c*. The kit can include a solid support coated with *B. burgdorferi* polyclonal antibodies which bind to at least one of the 31, 34, 39, and 93 kDa antigens of *B. burgdorferi*. The kit can also include 1) a container of lyophilized detection antibody-enzyme conjugate; 2) a measuring dispenser for dispensing patient body fluids, such as urine; and 3) a container having a chromogenic substrate and $H_2O_2$.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, body fluids other than urine can be used in the assay, such as blood, saliva, and cerebrospinal fluid. Any kind of detection antibody known in the art can be used. Any kind of indicator known in the art can be used. Color produced by the assay can be quantified by methods known in the art. The assay of the invention can be used to verify the efficacy of antibiotic or other therapy in the treatment of Lyme disease. The generation of the *B. burgdorferi* polyclonal antibodies which bind to the 31, 34, 39, and 93 kDa antigens can be performed by known methods other than inoculation of animals. The assay can be used to detect Lyme disease in animals as well as in humans.

It will be understood that various changes in the details, materials, and arrangements of the parts which have been described and illustrated above in order to explain the nature of this invention may be made by those skilled in the art without departing from the principle and scope of the invention as recited in the following claims.

I claim:

1. A method for detecting *Borrelia burgdorferi* antigens in urine samples, comprising:
   1) providing a capillary membrane lateral flow test assay strip having a first end a second opposite end; said assay strip comprising
      a. a reaction zone near said first end, wherein said reaction zone includes detection antibodies having an enzyme linked thereto, and further wherein said detection antibodies are capable of forming antigen-detection antibody complexes;
      a test zone near said second opposite end, wherein said test zone includes (i) polyclonal capture antibodies immobilized within said test zone that have reactivity to 39 kDa *B. burgdorferi* antigen, and (ii) a substrate;
   2) placing a urine sample on said first end of the assay strip;
   3) migrating said urine sample into the reaction zone, wherein said detection antibodies bind to *B. burgdorferi* antigens to form antigen-detection antibody complexes linked to the enzyme;
   4) migrating the urine sample into the test zone, wherein the antigen-detection antibody complexes linked to the enzyme engage the immobilized polyclonal capture antibodies, thereby causing the enzyme to convert the substrate to a visible or detectable product if 39 kDa *B. burgdorferi* antigens are present in the urine sample.

2. The method of claim 1 wherein said polyclonal antibodies are derived from animals hyper immunized with low passage strain B31 of *Borrelia burgdorferi*.

3. The method of claim 1 wherein said enzyme is horseradish peroxidase and said substrate is tetramethylbenzidine.

4. A method for detecting *Borrelia burgdorferi* antigens in a body fluid comprising:
   1) providing a solid support having polyclonal capture antibodies immobilized thereon, said polyclonal capture antibodies having reactivity against 39 kDa *B. burgdorferi* antigens in a body fluid;
   2) providing detection antibodies in a first container, said detection antibodies having an enzyme linked thereto;
   3) providing a substrate in solution in a second container;
   4) placing said body fluid in said first container;
   5) placing said solid support in said body fluid sample in said first container;
   6) removing said solid support from said first container, washing said solid support, and placing said solid support in the solution in the second container;
   7) producing a visible or detectable color in said second container by the action of said enzyme on said substrate if said *Borrelia burgdorferi* antigens are present in said body fluid sample.

5. The method of claim 4 wherein said polyclonal antibodies are derived from animals hyper immunized with low passage strain B31 of *Borrelia burgdorferi*.

6. The method of claim 4 wherein said enzyme is horseradish peroxidase and said chromogenic substrate is tetramethylbenzidine.

7. The method of claim 4 wherein said detection antibodies in said second container are lyophilized.

8. A method of detecting low levels of *Borrelia burgdorferi* antigens in a urine sample in the early stages of Lyme borreliosis comprising:
   a. obtaining a urine sample;
   b. contacting the urine sample with a test strip that comprises (i) a reaction zone including lyophilized detection antibodies, wherein said detection antibodies react with the antigens to form antigen-detection antibody complexes which migrate toward a test zone by capillary membrane action; and (ii) a test zone comprised of immobilized polyclonal capture antibodies having reactivity against 39 kDa *B. burgdorferi* antigens and a chromogenic substrate having reactivity with the detection antibodies; wherein the capture antibodies are bound to the antigen-detection antibody complexes and the detection antibodies react with the chromogenic substrate; and
   c. determining the presence of a visible color indicating the presence of 39 kDa *B. burgdorferi* antigens in the urine sample.

9. A lateral flow test assay test for the detection of low levels of *B. burgdorferi* antigens comprising 39 kDa antigens in a urine sample, comprising a test strip that includes:
   a. a reaction zone comprised of lyophilized detection antibodies, wherein said detection antibodies react with the antigens to form antigen-detection antibody complexes which migrate toward a test zone by capillary membrane action; and
   b. a test zone comprised of immobilized capture antibodies having reactivity against 39 kDa *B. burgdorferi* antigens and a chromogenic substrate having reactivity with the detection antibodies; wherein the capture antibodies are bound to the antigen-detection antibody complexes and the detection antibodies react with the chromogenic substrate to produce a visible color indicating the presence of 39 kDa *B. burgdorferi* antigens in the urine sample.

10. A handheld test kit for the detection of low levels of *Borrelia burgdorferi* antigens comprising 39 kDa antigens in a urine sample, comprising the test strip of claim 9.

* * * * *